United States Patent
Varghese et al.

(10) Patent No.: US 11,241,284 B1
(45) Date of Patent: Feb. 8, 2022

(54) SKIN TREATMENT DEVICE

(71) Applicant: KONINKLIJKE PHILIPS N.V., Eindhoven (NL)

(72) Inventors: Babu Varghese, Eindhoven (NL); Marco Baragona, Eindhoven (NL); Jonathan Alambra Palero, Eindhoven (NL); Martin Jurna, Eindhoven (NL); Margaret Ruth Horton, Eindhoven (NL); Anna Ezerskaia, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 389 days.

(21) Appl. No.: 15/781,186

(22) PCT Filed: Dec. 8, 2016

(86) PCT No.: PCT/EP2016/080300
§ 371 (c)(1),
(2) Date: Jun. 4, 2018

(87) PCT Pub. No.: WO2017/097923
PCT Pub. Date: Jun. 15, 2017

(30) Foreign Application Priority Data

Dec. 11, 2015 (EP) .................... 15199648

(51) Int. Cl.
*A61B 18/20* (2006.01)
*A61N 5/06* (2006.01)
(Continued)

(52) U.S. Cl.
CPC .......... *A61B 18/203* (2013.01); *A61N 5/0616* (2013.01); *A61B 2018/0047* (2013.01);
(Continued)

(58) Field of Classification Search
CPC .......... A61B 18/203; A61B 2018/2266; A61B 2018/0047; A61B 2018/2035; A61N 5/0616; A61N 2005/067
See application file for complete search history.

(56) References Cited

U.S. PATENT DOCUMENTS 4,995,691 A * 2/1991 Purcell, Jr. ............. G02B 6/421
385/29
5,808,657 A * 9/1998 Kurtz ....................... B41J 2/451
347/239

(Continued)

FOREIGN PATENT DOCUMENTS

| EP | 2305348 A1 | 4/2011 |
| WO | 2004037068 A2 | 5/2004 |
| WO | 2015110273 A1 | 7/2015 |

OTHER PUBLICATIONS

Markolf H. Niemz, "Laser-Tissue interactions," Springer publications, pp. 76-81 (1996).

(Continued)

*Primary Examiner* — Gary Jackson
*Assistant Examiner* — Sebastian X Lukjan

(57) ABSTRACT

The invention relates to a skin treatment device (10) for fractional treatment of the skin (100) of a human being. A radiation source (5) emits a multi-mode laser beam (20) with a superposition (23) of mutually different higher-order laser modes. The multi-mode laser beam is configured by said superposition of different laser modes to simultaneously cause a first plurality of high-intensity zones, where the thermal threshold (TC) for collagen denaturation for the treatment zone (50) of the skin is at least reached, and a second plurality of low-intensity zones where the thermal threshold (TF) for fibroblast stimulation for the treatment zone of the skin is at least reached. This is advantageous for obtaining a skin treatment device with a simple and there- (Continued)

fore low-cost fractional laser skin treatment system for combined collagen denaturation and fibroblast stimulation. The skin treatment device is based on non-uniform laser radiation in the form of the multi-mode laser beam.

13 Claims, 13 Drawing Sheets

(51) Int. Cl.
    *A61N 5/067*     (2006.01)
    *A61B 18/22*     (2006.01)
    *A61B 18/00*     (2006.01)

(52) U.S. Cl.
    CPC ............ *A61B 2018/2035* (2013.01); *A61B 2018/2266* (2013.01); *A61N 2005/067* (2013.01)

(56) References Cited

U.S. PATENT DOCUMENTS

| | | | |
|---|---|---|---|
| 5,908,416 A | 6/1999 | Costello | |
| 7,856,985 B2 | 12/2010 | Mirkov | |
| 8,246,611 B2 | 8/2012 | Paithankar | |
| 8,702,771 B1 | 4/2014 | Frost | |
| 2002/0013578 A1* | 1/2002 | Clement | A61B 18/203 606/9 |
| 2006/0212025 A1* | 9/2006 | McDaniel | A61N 5/0617 606/9 |
| 2006/0247609 A1* | 11/2006 | Mirkov | A61B 18/203 606/9 |
| 2007/0021807 A1* | 1/2007 | Kurtz | A61N 5/0616 607/88 |
| 2010/0145321 A1 | 6/2010 | Altshuler | |
| 2014/0321484 A1 | 10/2014 | Sierra | |

OTHER PUBLICATIONS

Tae Moon Jeong and Jongmin Lee, "Laser Pulse Phenomena and Applications," edited by F.J. Duarte, ISBN 978-953-1007-405-4.
G. Beir and J. Engel, "The Renaturation of Soluble Collagen. Products Formed at Different Temperatures," Biochemistry, vol. 5, No. 8, pp. 2744-2755, 1966.
S.D. Dams, M.de Liefde-van Beest, A.M. Nuijs, C.W.J. Oomens, F.P.T. Baaijens. Pulsed heat shocks enhance procollagen type I and procollagen type III expression in human dermal fibroblasts. Skin Research and Technology, 16(3): 354-364, 2010.
Dickey, Fred M., Scott C. Holswade, and David L. Shealy, eds. Laser beam shaping applications. CRC Press, 2005.
Manstein D, G.Scott Herron, R. Kehl Sink, Heather Tanner & R. Rox Anderson, "Fractional Photothermolysis: A New Concept for Cutaneous Remodieling Using Microscopic Patterns of Thermal Injury," Lasers Surg Med., 34, 426-438, (2004).
Misbah Huzaira Khan, R. Kehl Sink, Dieter Manstein, David Eimerl, R. Rox Anderson, "Intradermally Focused Infrared Laser Pulses: Thermal Effects at Defined Tissue Depths," Lasers in Surgery and Medicine 36:270-280 (2005).
Harris, D. M. et al in "Facial skin resurfacing with a very short pulsed CO2 laser: Beam characterization and initial histological results", Proceedings SPIE 2671, pp. 211-218 (1996). Mere mention of multi-mode CO2 laser for skin resurfacing.
Palomar, "StarLux Fractional Non-ablative Skin Resurfacing". Array of micro-beams create columns of coagulated tissue within the skin. No mention of the mode of laser beam.
Asadpour A. et al in "Fiber output beam shape study using imaging technique", J. of Appl. Science 10(4), pp. 312-318. (2010). Multimode fibers with speckle profiles for skin illuminations and scar therapies.

\* cited by examiner

SKIN TREATMENT DEVICE

This application is the U.S. National Phase application under 35 U.S.C. § 371 of International Application No. PCT/EP2016/080300, filed on Dec. 8, 2016, which claims the benefit of International Application No. 15199648.5 filed on Dec. 11, 2015. These applications are hereby incorporated by reference herein.

FIELD OF THE INVENTION

The invention relates generally to the treatment of skin of a human being, using a skin treatment device. The invention particularly relates to a device for performing this treatment.

BACKGROUND OF THE INVENTION

Laser skin rejuvenation is an intervention that generates new skin tissue by intentionally damaging the skin by optical means. In selective non-ablative photothermolysis based on water absorption, tissue is heated between 60 and 100° C. to create damaged thermal zones to induce new collagen growth, without ablation or vaporization of the skin.

In some home use devices, so-called fractional rejuvenation is often performed through the creation of distributed small lesions, typically 100-300 µm in size, surrounded by healthy tissue to minimize downtime and side effects while maintaining required efficacy levels. Thus, fractional laser treatment is a non-invasive treatment that uses a device to deliver a laser beam divided into many, e.g. thousands, microscopic treatment zones that can target a fraction of the skin at a time.

The cross-links that support the collagen fiber structure start breaking and collagen fibrils start to denature when heated above a temperature of 60° C. Within the reversible denaturing regime, the collagen is not permanently damaged, but rather stays intact and the denaturing can be reversed. This reversible denaturing threshold is very important, because it allows dermal collagen to be remodeled without creating permanent damage. When the temperature exceeds 100° C., other processes such as phase changes (vaporization, thermal decomposition (ablation), carbonization, and melting) will occur depending on the temperature. More details about the human skin interaction with laser can be found in Markolf H. Niemz, "*Laser-Tissue interactions*," Springer publications (1996).

An alternative method for skin rejuvenation is to heat the dermis to relatively low temperatures in the range of 39 and 45° C. to stimulate the dermal cells to release heat-shock proteins (HSP). The release of HSP promotes new collagen and elastin formation, new cell formation and collagen reconfiguration. In addition to its thermal effect, the laser may also evoke a photochemical effect.

U.S. Pat. No. 7,856,985 B2 (assigned to Cynosure Inc.) discloses an apparatus for laser treatment, such as skin rejuvenation treatment, using non-uniform laser radiation. A high-intensity portion of the laser radiation causes collagen destruction and shrinkage within select portions of the treatment area, while a lower-intensity portion of the radiation causes fibroblast stimulation leading to collagen production across other portions of the treatment area. An output beam from a laser source, such as an Nd:YAG laser, is coupled into an optical system that modifies the beam to provide a large-diameter beam having a non-uniform energy profile, comprised of a plurality of high-intensity zones surrounded by lower-intensity zones within the treatment beam. The higher-intensity zones heat select portions of the target tissue to temperatures sufficient for a first treatment (e.g. collagen shrinkage), while the lower-intensity zones provide sufficient energy for a second treatment (e.g. stimulated collagen production). A large area of tissue, preferably 7-10 mm in diameter, can be treated simultaneously, while minimizing the risk of burning or other damage to the skin. In one embodiment, the invention uses a fiber bundle to provide a non-uniform energy output beam. In another embodiment, the invention uses a diffractive lens array to produce the non-uniform output beam. Thus, this teaching combines collagen shrinkage in some zones with stimulation of collagen production in other zones. However, the optical design requires relative expensive optical components such as a diffractive lens array, or extensive fiber bundles and is therefore not attractive for low-cost home use skin treatment devices. Furthermore, the width of the smallest lesion may be relatively larger because of the inter-fiber distance in the fiber bundles.

The inventor of the present invention has appreciated that an improved and/or simpler skin treatment device is of benefit, and has in consequence devised the present invention.

SUMMARY OF THE INVENTION

It would be advantageous to achieve an improved and/or simpler skin treatment device. In general, the invention preferably seeks to mitigate, alleviate or eliminate one or more of the above mentioned disadvantages singly or in any combination. In particular, it may be seen as an object of the present invention to provide a skin treatment device that solves the above mentioned problems, or other problems, of the prior art.

To better address one or more of these concerns, in a first aspect of the invention, there is provided a skin treatment device for fractional treatment of the skin of a human being, the skin treatment device comprising:

a radiation source capable of emitting a multi-mode laser beam, and a radiation control unit for controlling the radiation source, wherein the radiation source and the radiation control unit are optically arranged so that the multi-mode laser beam, when impinging on a treatment zone of the skin, is spatially configured so as to simultaneously create:

a first plurality of high-intensity zones wherein a thermal threshold (TC) for collagen denaturation for said treatment zone of the skin is at least reached, and a second plurality of low-intensity zones wherein a thermal threshold (TF) for fibroblast stimulation for said treatment zone of the skin is at least reached, but wherein said thermal threshold (TC) for collagen denaturation is not reached, wherein the multi-mode laser beam substantially only comprises a superposition of only higher-order laser modes which are mutually different, the higher-order laser modes having mutually different intensity profiles in a beam cross-section transverse to a propagation direction of the laser beam, and wherein the radiation source and the radiation control unit are configured so that a Lagrange value (H) of the multi-mode laser beam, when leaving the skin treatment device, is at least 0.5µ, preferably at least 1µ, more preferably at least 5µ.

The invention is particularly, but not exclusively, advantageous for obtaining a skin treatment device with a simple and therefore low-cost fractional laser skin treatment system for combined collagen denaturation and fibroblast stimulation in a single treatment device based on non-uniform laser radiation in the form of the multi-mode laser beam.

In the light of the present invention, the expression "the multi-mode laser beam substantially only comprises a superposition of only higher-order laser modes which are mutually different" has to be interpreted such that the multi-mode laser beam mainly comprises a superposition of at least two higher-order laser modes, and that the multi-mode laser beam does not comprise any substantial fundamental laser mode components (e.g. HG00). In particular, the part of the overall intensity of the total intensity profile of the laser beam cross-section attributable to the presence of any (e.g. naturally remaining) fundamental laser mode components in the total intensity profile should be smaller than 10%, preferable smaller than 5%. Advantageously, the multi-mode laser beam only comprises a superposition of only higher-order laser modes. The invention is based on the insight that the intensity minima in the intensity profile of the superposition of only the higher-order laser modes can have sufficient intensity to reach the thermal threshold for fibroblast stimulation, without reaching the thermal threshold for collagen denaturation, while simultaneously the intensity maxima in the intensity profile of the superposition of only the higher-order laser modes can have sufficient intensity to reach the thermal threshold for collagen denaturation, without reaching any higher thermal thresholds which lead to unwanted ablation and other unwanted side effects. According to the invention, the intensity profile of the multi-mode laser beam comprising said superposition has an optimum distribution of high-intensity and low-intensity zones for generating the zones of collagen denaturation and fibroblast stimulation in the treatment zone of the skin.

Thus, the above mentioned multi-mode laser beam is capable of heating the target tissue of the skin to temperatures sufficient for collagen denaturation and shrinkage in the said high-intensity zone (e.g. 60-100° C.), whereas a lower-intensity portion of the multi-mode laser beam causes the surrounding tissue in the said low-intensity zones to heat up to relatively lower temperatures (39-45° C.) causing fibroblast stimulation (leading to neocollagenesis) across other portions of the treatment area. This will result in a plurality of sub-fractional zones of central zones of collagen denaturation and shrinkage, resulting from high intensity peaks, surrounded by zones of fibroblast stimulation leading to collagen production due to the relatively lower intensity of laser energy in the low-intensity zones. This will in turn result in faster healing of the lesion due to the increased number of thermal zones surrounding fibroblast stimulated zones.

The invention is further, but not exclusively, advantageous in that a relatively larger area of tissue, i.e. a treatment zone preferably 10-20 mm in spatial extension, e.g. diameter or maximum transverse width, may be treated simultaneously, for example in an unfocused geometry, with the lens.

Within the context of the present invention, it is to be understood that the term 'fractional skin treatment' may be considered to include, but not to be limited to, skin treatment performed by the parallel treatment of a distributed array of small lesions or areas in the skin, typically 50-500 μm, or preferably 100-300 μm, in size. In the context of the present invention, these small lesions created in the high-intensity zones are further surrounded by the low-intensity zones where fibroblast stimulation takes place. The small lesions created in the high-intensity zones are in the field sometimes referred to as 'hot spots' due to their higher temperature.

In a particularly advantageous embodiment, the superposition of higher-order laser modes results in a combined intensity profile of the multi-mode laser beam, with one, or more, non-zero minima (MIN) corresponding to one, or more, low-intensity zones in said second plurality of low-intensity zones, which provides a surprisingly efficient and simple way of facilitating fibroblast stimulation in a relatively large treatment zone.

In another advantageous embodiment, the superposition of higher-order laser modes results in a combined intensity profile of the multi-mode laser beam, with one, or more, maxima (MAX) corresponding to one, or more, high-intensity zones in said first plurality of high-intensity zones, thereby also providing a surprisingly efficient and simple way of facilitating collagen denaturation in a relatively large treatment zone.

Advantageously, the multi-mode laser beam, when impinging on the treatment zone of the skin, may be spatially configured by said superposition of higher-order laser modes so as to form a coherent treatment zone of the skin, wherein preferably the thermal threshold (TF) for fibroblast stimulation is at least reached substantially throughout said coherent treatment zone of the skin. This provides a more effective way of treating the skin because of faster healing of the skin lesions due to the increased number of surrounding fibroblast stimulated zones.

Advantageously, the first plurality of high-intensity zones and the second plurality of low-intensity zones may be spatially distributed in the treatment zone so that, when the multi-mode laser beam impinges on the treatment zone of the skin, a thermal profile is induced wherein the temperature gradually decreases from the high-intensity zones to any neighboring low-intensity zones surrounding the high-intensity zones, and wherein the temperature preferably—approximately or substantially—continuously decreases from the high-intensity zones to the neighboring low-intensity zones. This is quite different from many existing skin treatment technologies, where treatment is performed in so-called hot spots with no, or little, fibroblast stimulation around these hot spots.

In some embodiments, the skin treatment device further comprises a lens for directing the multi-mode laser beam onto the skin. Additionally or alternatively, the radiation source and the radiation control unit for controlling the radiation source are configured so that a number (N) of different higher-order laser modes of the superposition is at most 10, preferably at most 7, more preferably at most 5, because of the overall decrease in intensity with an increasing number of modes, as the skilled person in optics will recognize. Below, more specific calculations for various modes are presented.

For providing an optimum treatment of the skin in embodiments which further comprise a lens for directing the multi-mode laser beam onto the skin, the radiation source, the radiation control unit for controlling the radiation source, and the lens may be collectively arranged so that a maximum spatial extension of the treatment zone is at least 10 mm, preferably at least 15 mm, more preferably at least 20 mm.

Preferably, said superposition of higher-order laser modes comprises at least two mutually different kinds of higher-order laser modes selected from:

rectangular transverse Hermite-Gaussian modes HG[m n], wherein m and n are mode numbers, or cylindrical transverse Laguerre-Gaussian modes LG[p l], wherein p and l are mode numbers, and wherein each of the mode numbers, [m n] or [p l], is below 8, preferably below 6, more preferably below 4. Other feasible higher-order laser modes are also contemplated within the teaching and principle of the present invention, as the skilled person in optics will recognize.

Beneficially, in embodiments which further comprise a lens for directing the multi-mode laser beam onto the skin, the lens may have an adjustable focal point for changing the position, extension and/or orientation of the treatment zone in the skin, e.g. for delivering the best way of skin treatment.

In a particular embodiment, the radiation source comprises a plurality of lasers controllable by the radiation control unit, each laser being capable of emitting a multi-mode laser beam, each multi-mode laser beam substantially only comprising a superposition of only higher-order laser modes with mutually different intensity profiles in a beam cross-section transverse to a propagation direction of the laser beam. Typically, in embodiments further comprising a lens for directing the multi-mode laser beam onto the skin, the multi-mode laser beams emitted from the plurality of lasers may have a common optical path from the radiation source to the lens to provide a simple and cost-effective optical configuration. It is to be understood that the optical path may be common almost all the way from the radiation source to the lens, but may slightly differ, at least in the beginning of the optical path, due to the lasers originating at different locations.

Furthermore, said plurality of lasers controllable by the radiation control unit may be optically arranged so as to create a common treatment zone in the skin, or, alternatively, the plurality of lasers controllable by the radiation control unit may be optically arranged to create at least two different treatment zones in the skin, each treatment zone having:

a first plurality of high-intensity zones wherein the thermal threshold (TC) for collagen denaturation for said treatment zone of the skin is at least reached, and a second plurality of low-intensity zones wherein the thermal threshold (TF) for fibroblast stimulation for said treatment zone of the skin is least reached, but wherein said thermal threshold (TC) for collagen denaturation is not reached.

Thus, a large portion of skin may be treated if a plurality of lasers are applied in the context of the present invention.

In another embodiment, the radiation source comprises a single laser capable of emitting a multi-mode laser beam, the laser beam substantially only comprising a superposition of only higher-order laser modes which are mutually different, the higher-order laser modes having mutually different intensity profiles in a beam cross-section transverse to a propagation direction of the laser beam, possibly providing a simple and cost-effective way of implementing the invention, yet being capable of treating a relatively large area of skin.

The skin treatment device according to the present invention may be used in a method for non-invasive fractional treatment of the skin of a human being, the skin treatment method comprising:

providing a radiation source capable of emitting a multi-mode laser beam, the laser beam substantially only comprising a superposition of only higher-order laser modes which are mutually different, the higher-order laser modes having mutually different intensity profiles in a beam cross-section transverse to a propagation direction of the laser beam, and providing a radiation control unit for controlling the radiation source, wherein the radiation source and the radiation control unit are optically arranged so that the multi-mode laser beam, when impinging on a treatment zone of the skin, is spatially configured by said superposition of said higher-order laser modes so as to simultaneously cause:

a first plurality of high-intensity zones wherein the thermal threshold (TC) for collagen denaturation for said treatment zone of the skin is at least reached, and a second plurality of low-intensity zones wherein the thermal threshold (TF) for fibroblast stimulation for said treatment zone of the skin is at least reached, but wherein said thermal threshold (TC) for collagen denaturation is not reached.

The skin treatment device according to the invention is particularly, but not exclusively, advantageous for providing a method for skin treatment in a simple and therefore low-cost manner, for example by modifying hitherto known laser skin treatment devices for implementing the present invention, and/or for combining various optical elements to implement the invention.

In general, the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

It should be noted that items bearing the same reference numbers in different Figures have the same structural features and the same functions, or represent the same signals. Where the function and/or structure of such an item has been explained, there is no necessity for repeated explanation thereof in the detailed description.

DETAILED DESCRIPTION OF THE EMBODIMENTS

Figure 1:
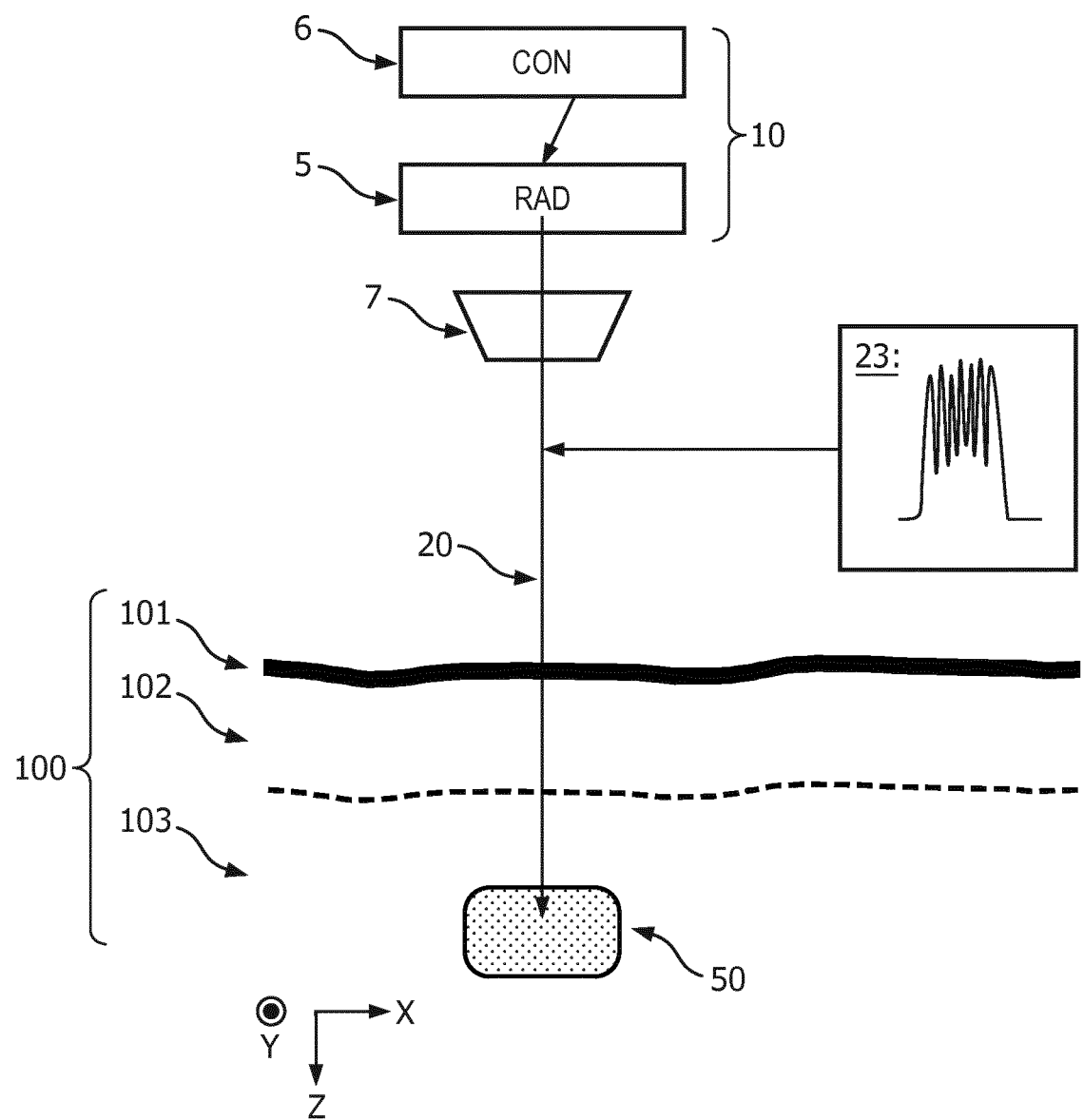
FIG. 1 shows a schematic cross-sectional drawing of a skin treatment device according to an embodiment of the invention.

FIG. 1 shows a schematic cross-sectional drawing of a skin treatment device 10 according to an embodiment of the invention. The skin treatment device 10 is configured and arranged for fractional treatment of the skin 100 of a human being, although non-human skin may also be treated in some variants. The skin treatment device 10 may be a single entity for convenient use. The skin 100 of a human is normally considered to have three parts, the upper stratum corneum 101, the epidermis 102, and the dermis 103. In the shown embodiment, the laser beam 20 is directed, e.g. focused, to the dermis 103, where a treatment zone 50 is shown, but any part, or combination, of the skin 100 may be treated according to the present invention, see FIG. 6. More details about human skin interaction with laser can be found in Markolf H. Niemz, "Laser-Tissue interactions", Springer publications (1996), which is hereby incorporated by reference in its entirety. For an overview of the effect of the temperature on tissue the Table below may be useful:

| | |
|---|---|
| 37° C. | Physiological temperature |
| 45° C. | Hyperthermia |
| 50° C. | Reduction in Enzyme activity, Cell immobility |
| 60° C. | Denaturation of collagen and proteins, Coagulation |
| 80° C. | Permeabilization of membranes |
| 100° C. | Vaporization, Thermal decomposition (ablation) |
| >150° C. | Carbonization |
| >300° C. | Melting |

As seen in FIG. 1, the skin treatment device comprises a radiation source 5 'RAD' capable of emitting a multi-mode laser beam 20. Thus, the resulting laser beam has a superposition 23 of different laser modes, the laser modes having different intensity profiles transverse to the beam direction. In the insert, the combined intensity profile transverse to the laser beam is shown. Furthermore, a radiation control unit 6 'CON' for controlling the radiation source is operably connected to the radiation source 5 for controlling, e.g. with respect to safety, user settings, etc. A lens 7 may be provided in the device 10 for directing the multi-mode laser beam onto the skin; the lens may have an adjustable focal point and/or numerical aperture (NA) for changing the position, extension and/or orientation of the treatment zone in the skin 100. The lens can also be controlled by the control unit 6. When the multi-mode laser beam 20 impinges on the treatment zone 50 of the skin 10, preferably in pulsed mode, the laser beam is particularly spatially configured by said superposition 23 of mutually different higher-order laser modes so as to simultaneously cause a first plurality of high-intensity zones 30 where the thermal threshold TC for collagen denaturation, or similar thermally induced processes, for said treatment zone of the skin is at least reached, and a second plurality of low-intensity zones 40 where the thermal threshold TF for fibroblast stimulation, or similar thermally induced processes, for said treatment zone of the skin is at least reached. However, in the low-intensity zones the temperature is lower than in the high-intensity zones so that said thermal threshold (TC) for collagen denaturation is not reached in the low-intensity zones.

The skin treatment device can be operated preferably in a step-and-glide mode. In all embodiments, index-matching fluid can be used to optically couple the laser beam into the skin 100. The focusing depth at which thermal lesions can be created inside skin 100 can be varied by changing the numerical aperture NA and/or focusing depth of the focusing optical element, e.g. the lens 7. It may also be advantageous to use the invention together with other measures known in the art, such as surface cooling, a capacitance sensor to detect skin contact and enable skin treatment, as the skilled person in optics-based skin treatment will readily understand, once the general principle and teaching of the present invention is comprehended.

For ease of reference, an XYZ-coordinate system is shown in FIG. 1 and used in connection with the figures in this application. The Z-axis is parallel to the direction of the multi-mode laser beam 20, and the X-Y plane is transverse or perpendicular to the Z-axis.

Figure 2:
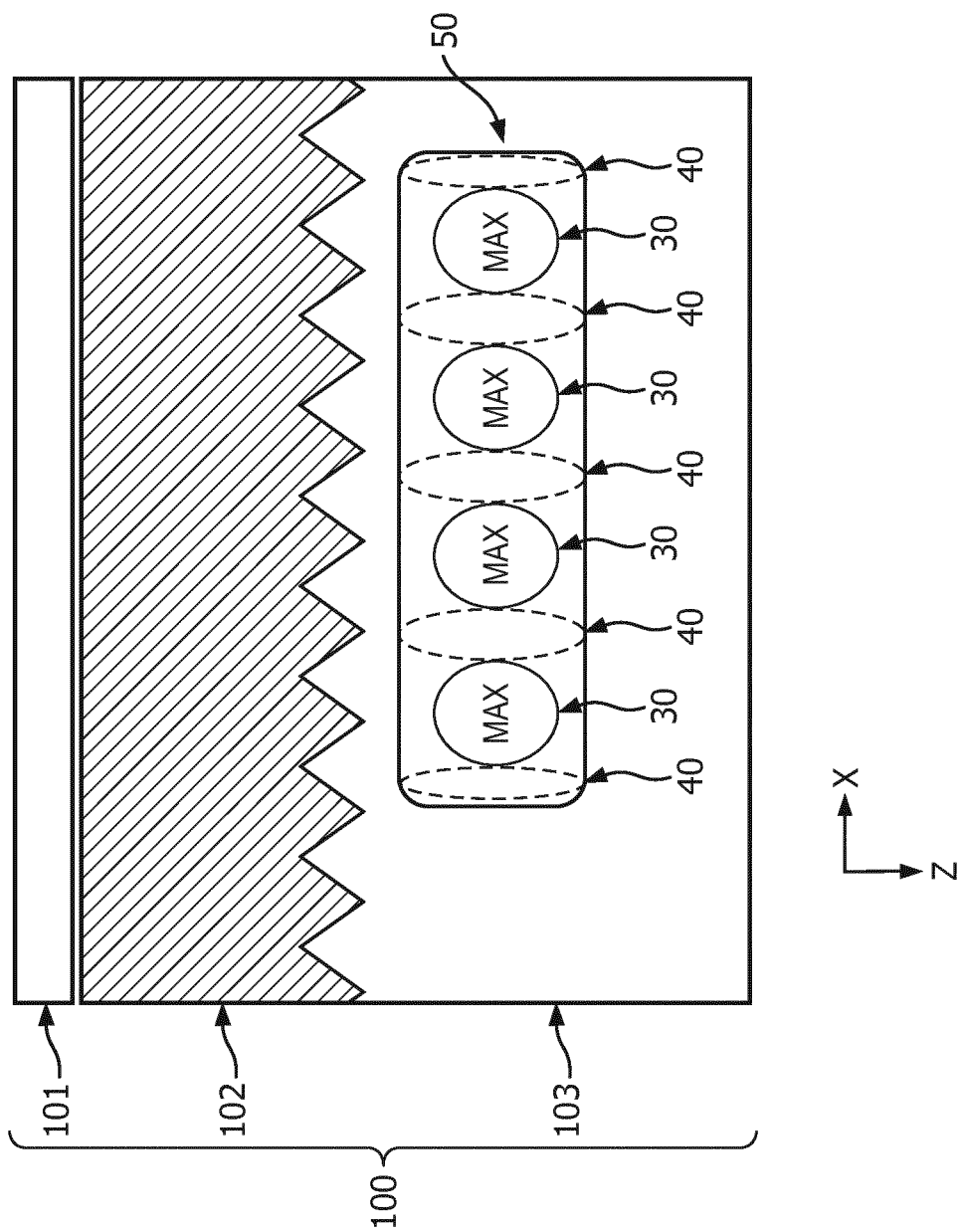
FIG. 2 shows a schematic cross-sectional drawing of a treatment zone in the skin when treated with a skin treatment device according to an embodiment of the invention.

FIG. 2 shows a schematic cross-sectional drawing of a treatment zone 50 in the skin 100 when treated with a skin treatment device according to an embodiment of the invention. The multi-mode laser beam—when impinging on a treatment zone 50 of the skin—is spatially configured by said superposition of at least two mutually different laser modes so as to simultaneously cause a combination of high-intensity zones 30 'MAX' and low-intensity zones 40 (dotted circles) in the skin. In FIG. 2, the low-intensity zones 40 shown in dotted circles are isolated from each other. Alternatively, the low-intensity zones described here may be continuous. This means that isolated high-intensity zones 30 'MAX' can also be embedded in a single continuous low-intensity zone 40. In the first plurality of high-intensity zones 30, the thermal threshold TC for collagen denaturation, or similar thermally induced processes, for said treatment zone of the skin is at least reached, and the temperature is in a range of around 60-100° C. In the second plurality of low-intensity zones 40, the thermal threshold TF for fibroblast stimulation, or similar thermally induced processes, for said treatment zone of the skin is at least reached. Thus, in the low-intensity zones, the temperature is at least high enough to induce fibroblast stimulation, and in some parts of the low-intensity zones 40, the temperature will be higher than the thermal threshold TF for fibroblast stimulation. Typically, the temperature will have a minimum during the laser treatment corresponding to the lowest beam intensity, and the temperature will increase towards the neighboring high-intensity zones 30 'MAX'. It is to be understood that the temperature profile will have a three-dimensional structure in the skin tissue 100, only the ZX projection being schematically indicated in FIG. 2. The combined volume or zone of treatment 50 comprises the low 40 and high 30 intensity zones, but the treatment zone may also comprise volume not being part of low 40 and high 30 intensity zones. In some embodiments, the multi-mode laser beam, when impinging on a treatment zone of the skin, is spatially configured by said superposition 23 of higher-order laser modes so as to form a coherent skin treatment zone 50, as shown in FIG. 2. In other embodiments, at least the thermal threshold (TF) for fibroblast stimulation is at least reached substantially throughout said coherent skin treatment zone, but this is not shown in FIG. 2.

Figure 3:
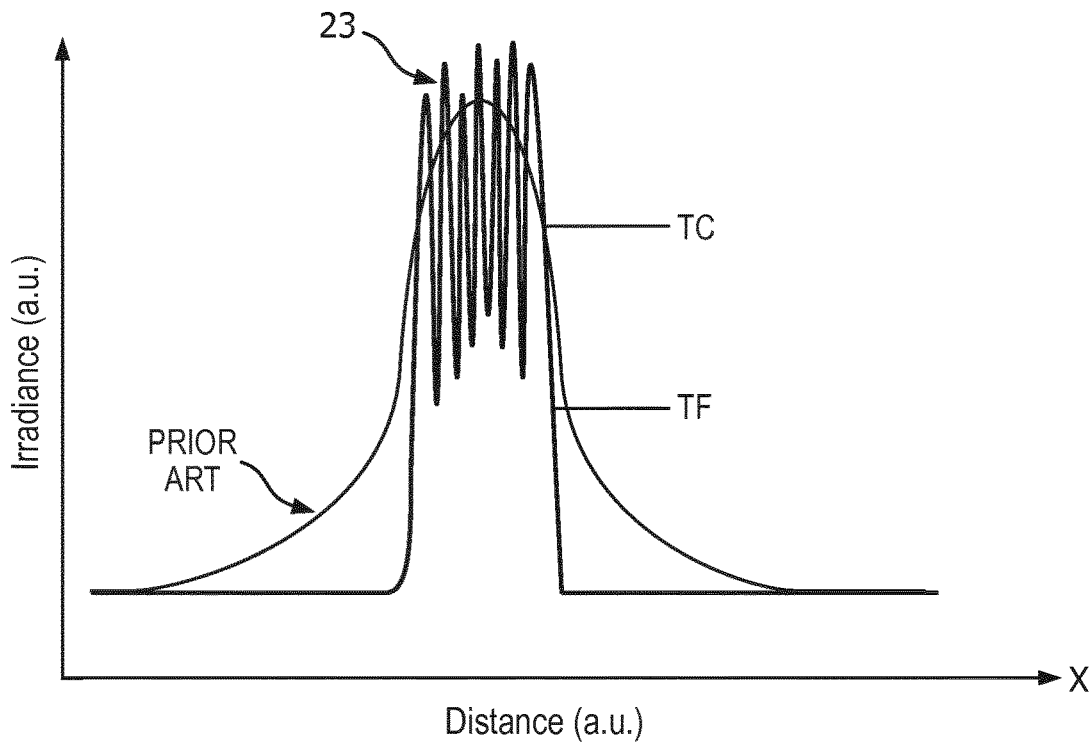
FIG. 3 shows a schematic graph of a transverse intensity or irradiance profile of a multi-mode laser beam from a skin treatment device according to an embodiment of the invention.

FIG. 3 shows a schematic graph of a transverse intensity or irradiance profile of multi-mode laser 23 together with a prior art Gaussian intensity profile labelled 'PRIOR ART'. The prior art teachings using Gaussian beam profiles tend to produce a relatively large single lesion based on photo-thermal effects. In prior art laser-based non-ablative treatment devices, a stimulation region can be expected to be present, since the region surrounding a damaged zone has been inherently subjected to temperatures below the damage threshold. This is because laser beam profiles normally do not have very sharp edges, e.g. Gaussian beam profiles, and this results in intensity gradients in the tissue and thus thermal gradients. Around the center of the beam, denaturation occurs depending on the time-temperature (governed by a damage integral), and in the vicinity close to the damaged zones, tissues are exposed to temperatures that do not reach damage levels but rather stimulation levels, resulting in a relatively large lesion surrounded by a small fibroblast stimulation zone. Because of the limited size of the fibroblast stimulation zone, the rejuvenation effect is limited in the prior art teachings.

Based on the effects described above, for laser-based skin rejuvenation, it would therefore be better to have more fibroblast stimulated tissue obtained by exposure to the multi-mode laser beam from a skin treatment device according to the present invention. This would extend the area of skin that is rejuvenated, while reducing the side effects of the injury.

Figure 4A:
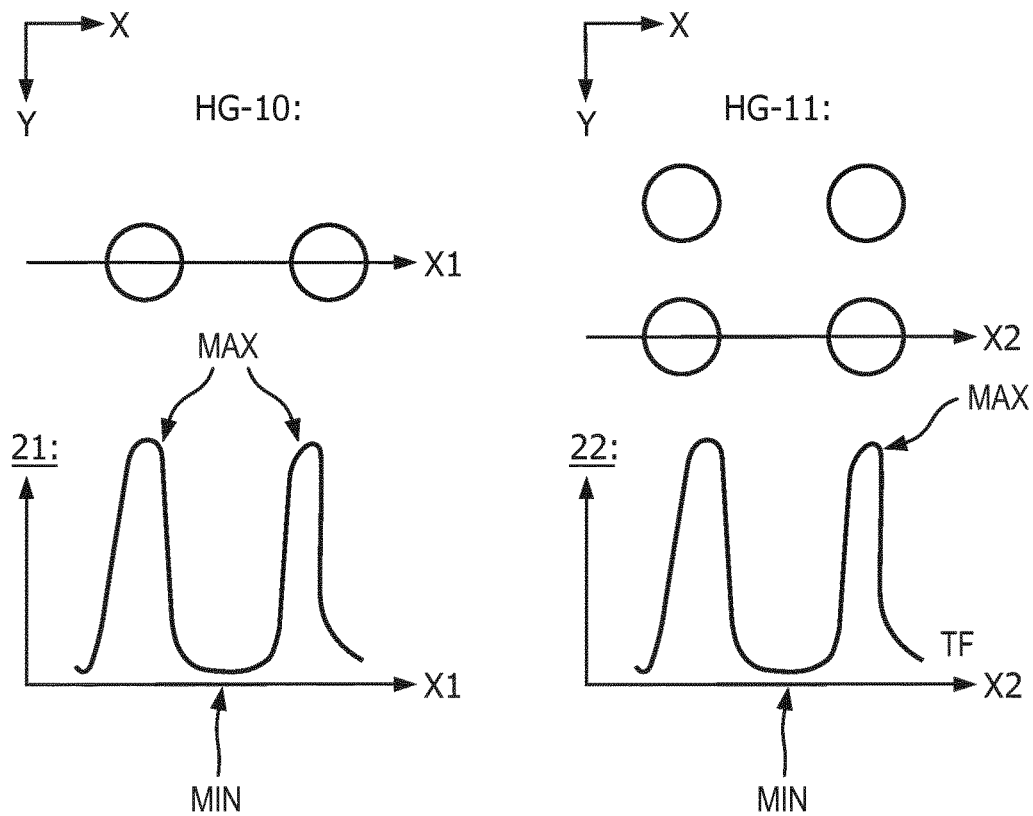
FIGS. 4A and 4B show schematic illustrations, and intensity profiles, of two modes of a laser beam, and a superposition of laser modes from a skin treatment device according to an embodiment of the invention.

FIG. 4A shows schematic illustrations of transverse intensity profiles 21 and 22 of modes HG-10 and HG-11 in a cross-section of a laser beam. To the right, the HG-10 mode is shown, and to the left is shown a HG-11 mode. Notice how the intensity profiles 21 and 22 have minima MIN close to zero (or approximately zero).

Figure 4B:
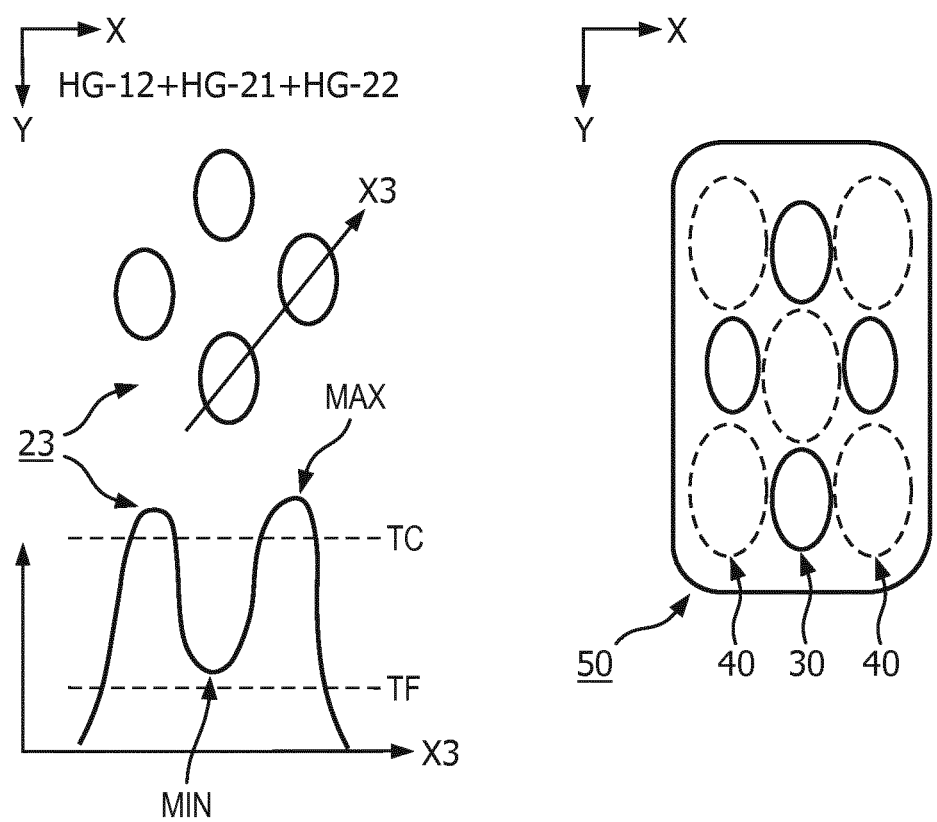

FIG. 4B shows the superposition 23 of HG-12, HG-21 and HG-22. The transverse intensity profile of the superposition 23 will also have minima MIN and maxima MAX in the intensity profiles, but actually one, or more, minima MIN in the superposition 23 is non-zero and, if designed appropriately, the superposition may have a resulting level of intensity at the minima MIN which is above the thermal threshold TF (horizontal dotted line) for fibroblast stimulation. Thus, the invention is based on the insight that the minima MIN in the intensity-profile of the superposition 23 of the higher-order laser modes, here HG-12, HG-21 and HG-22, can have sufficient intensity, or power, resulting in the thermal threshold for fibroblast stimulation TF being reached and preferably being above the threshold for facilitating further fibroblast simulation. This is schematically shown to the right in FIG. 4B, where the low intensity zones 40 and high intensity zones 30 are shown in a XY cross-sectional view, i.e. perpendicular to the corresponding view in FIG. 2.

Figure 5:
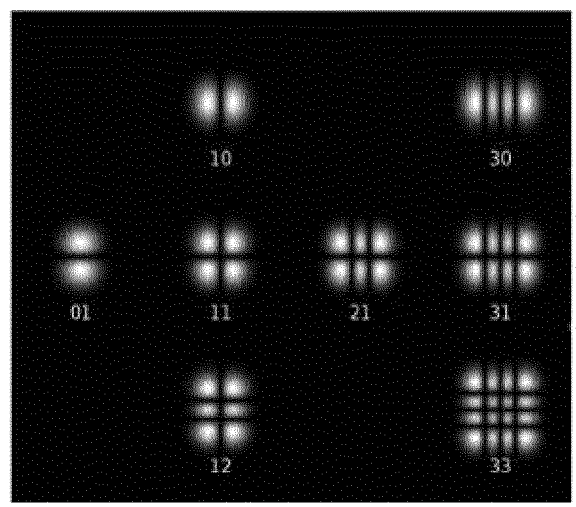
FIG. 5 shows examples of known rectangular (upper part) and cylindrical (lower part) transverse laser modes that may be applied with a skin treatment device according to an embodiment of the invention.
Figure 5:
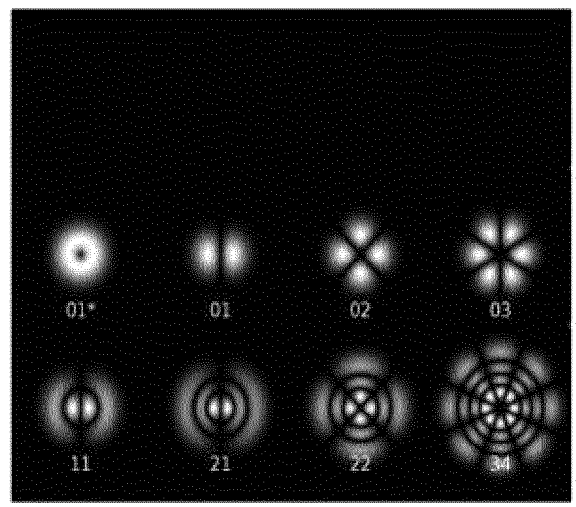

FIG. 5 shows an example of a known rectangular (upper part) and cylindrical (lower part) transverse laser mode that may be applied using a skin treatment device according to an embodiment of the invention. FIG. 5 (upper part) depicts examples of known Hermite-Gaussian modes that may be used, such as HG-01, HG-10 or HG-11. FIG. 5 (lower part) depicts examples of known Laguerre-Gaussian modes that may be used in the context of the present invention, such as LG-01, LG-02 and LG-03. In this patent application, the standard notation for LG modes is used—the first index indicates the number of radial mode orders (p), and the second index indicates the number of angular mode orders (l). More details on intensity distributions in higher-order laser modes can be found in Chapter 11: *Laser Beam Diagnostics in a Spatial Domain* by Tae Moon Jeong and Jongmin Lee, in the book *Laser Pulse Phenomena and Applications*, edited by F. J. Duarte, ISBN 978-953-1007-405-4. In FIG. 5, the separate Hermite-Gaussian mode (lower part) or Laguerre-Gaussian mode (upper part) can be used in combination or superposition for implementing the invention. It will be clear to the skilled person that suitable superpositions of intensity profiles may be created by a combination of modifications and/or optical elements within the laser cavity, and optical elements disposed along the optical path outside the laser cavity, as it will be understood once the general principle and teaching of the present invention is comprehended.

Figure 6:
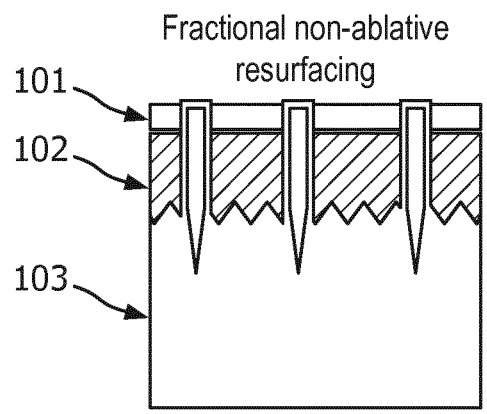
FIG. 6 shows four schematic cross-sectional drawings of treatment zones in the skin according to the prior art (part a and b), and when applying a skin treatment device according to embodiments of the invention (part c and d)
Figure 6:
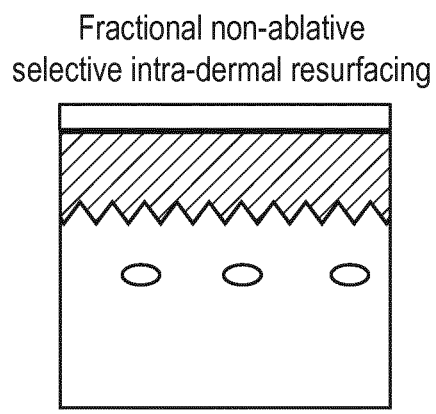
Figure 6:
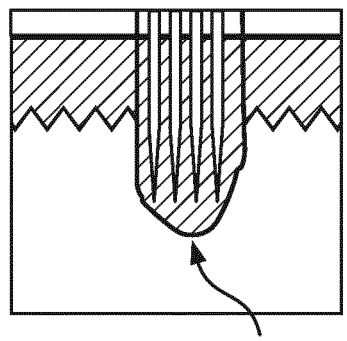
Figure 6:
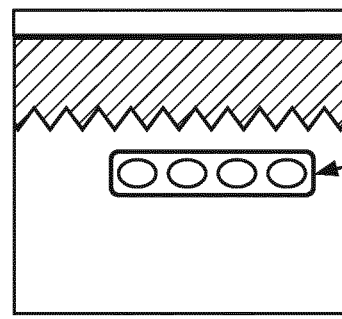

FIG. 6 shows four schematic cross-sectional drawings of treatment zones in the skin according to the prior art (part a and b), and when applying a skin treatment device according to two embodiments of the invention (part c and d). A schematic representation is given in part a) of fractional lesions in a non-ablative treatment and in part b) of a selective intra-dermal rejuvenation treatment. It is seen that a non-coherent treatment zone is obtained and the fibroblast stimulated areas are limited to relatively small areas surrounding these 'hot spots'. However, as seen in the schematic representations of sub-fractional zones consisting of central zones of collagen denaturation and shrinkage, resulting from high intensity peaks, surrounded by fibroblast stimulation zones, resulting from low intensity peaks, in a non-ablative treatment (c) and a selective intra-dermal resurfacing treatment (d) as disclosed in the present invention, there will be a relatively larger treatment zone 50, preferably a coherent treatment zone.

Figure 7:
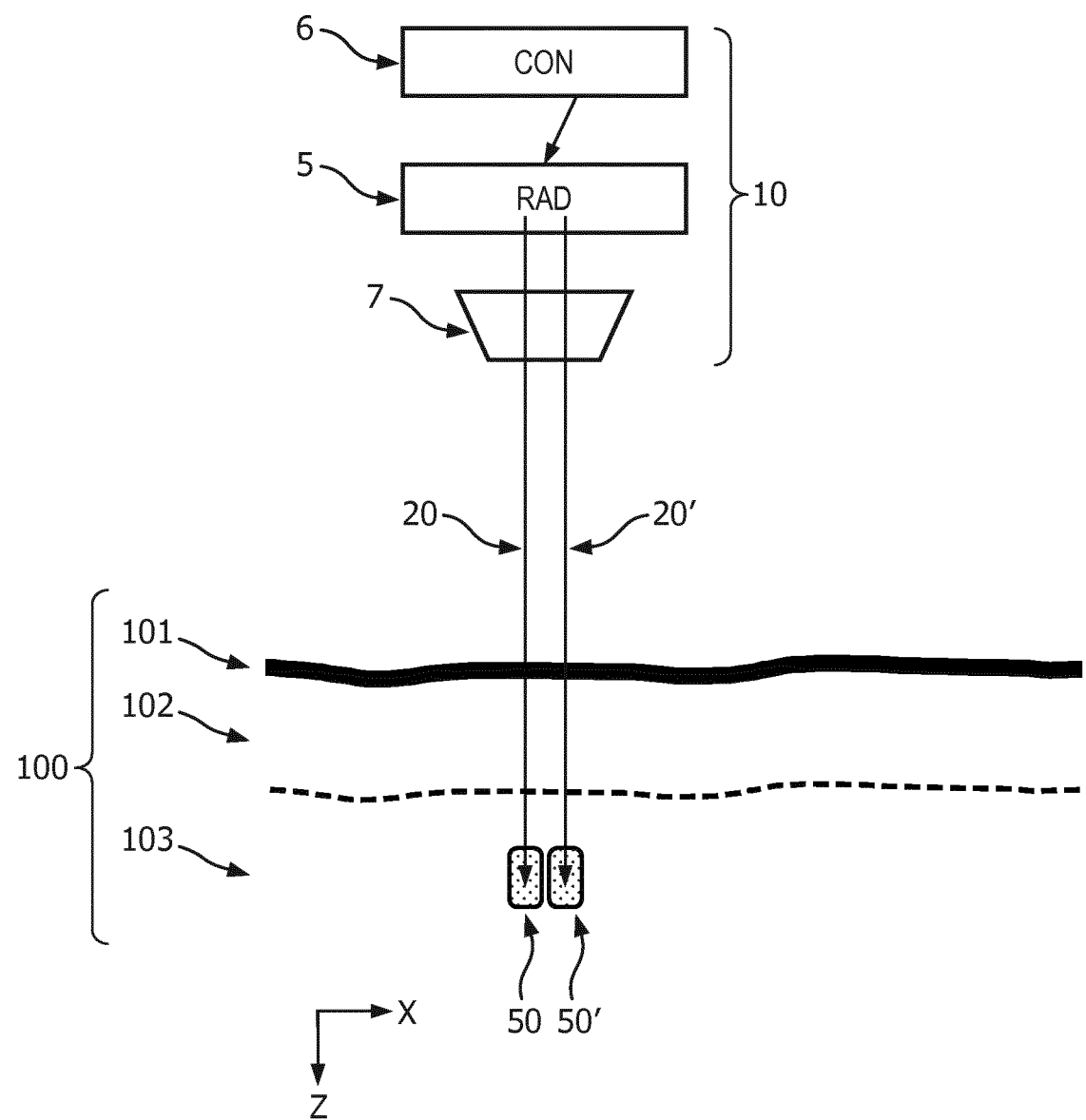
FIG. 7 shows a schematic cross-sectional drawing of a skin treatment device according to another embodiment of the invention.

FIG. 7 shows a schematic cross-sectional drawing of another skin treatment device according to another embodiment of the invention. The device is similar to the skin treatment device shown in FIG. 1, but an additional laser beam 20' is present. The additional laser beam is preferably also a multi-mode laser beam identical or similar to, or different from, the laser beam 20'. In a preferred embodiment, the laser beams 20 and 20' are identical and. more preferably, an array of similar lasers may be provided and controlled in the radiation source 5. In FIG. 7, the multi-mode laser beam 20' results in a neighboring and different treatment zone 50', but in other embodiments the laser beams 20 and 20' could result in one common treatment zone where thermally induced skin modifications are obtained from the skin treatment device 10.

Figure 8:
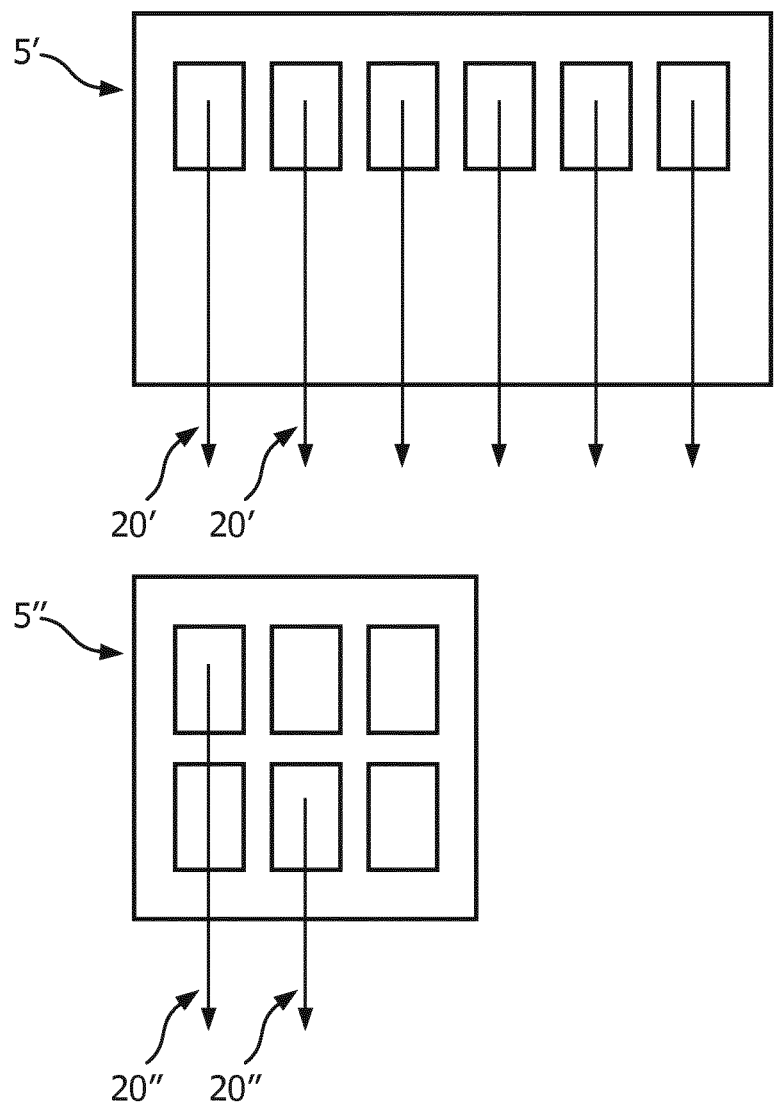
FIG. 8 shows a schematic drawing of two different radiation sources according to embodiments of the invention.

FIG. 8 shows a schematic drawing of two different radiation sources 5' and 5" according to embodiments of the invention. In the upper part, the lasers are arranged in linear, side by side configuration, preferably as closely spaced as possible to obtain a common treatment zone from the lasers, or adjacent treatment zones 50 and 50', as closely spaced as possible like in FIG. 7. In the lower part, the lasers are arranged in a matrix configuration, with the lasers being positioned in two dimensions, i.e. the XY-plane of FIG. 1, and preferably also as closely spaced as possible in both dimensions to obtain a common treatment zone from the lasers, or adjacent treatment zones.

Figure 9:
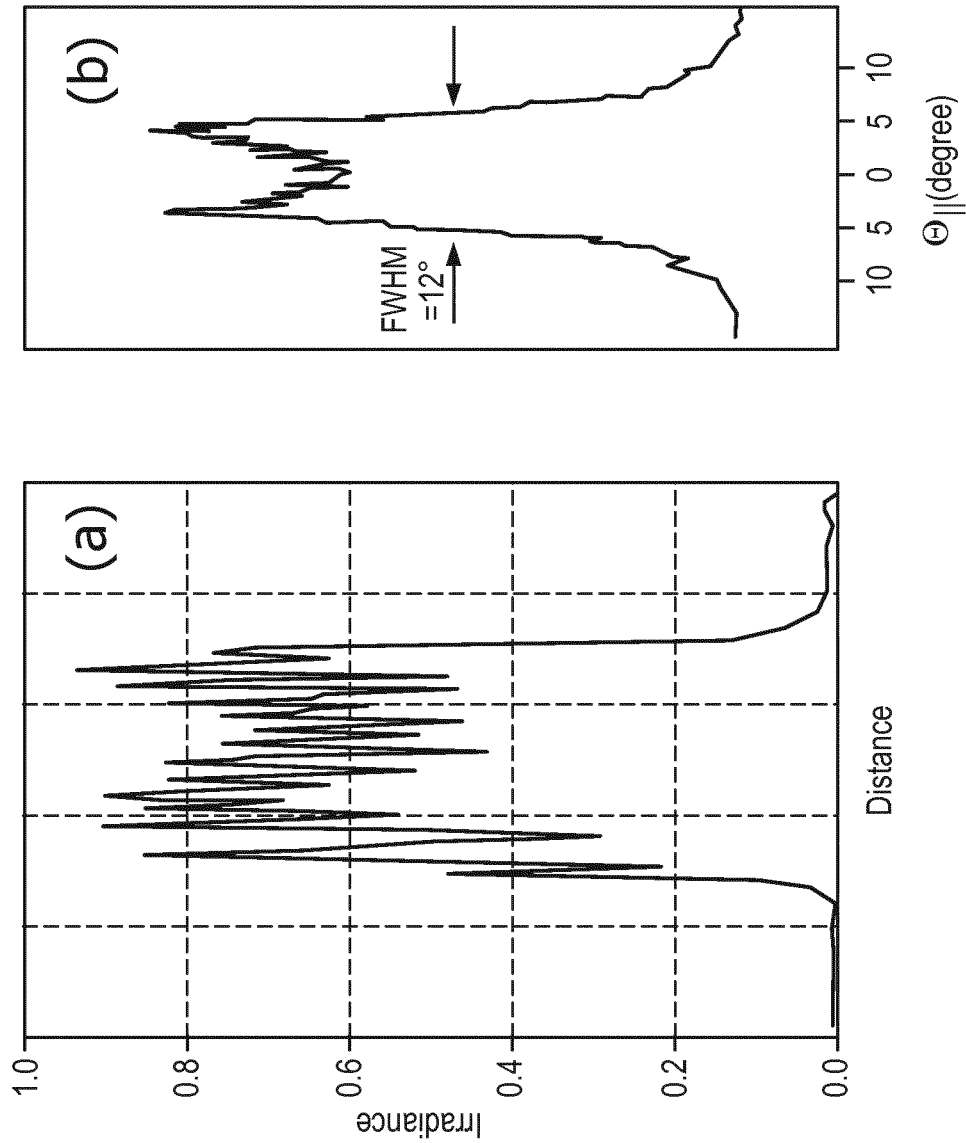
FIG. 9 shows the near field (a) and far field (b) intensity distribution of a multi-mode emitter for application in a skin treatment device according to an embodiment of the invention.

FIG. 9 shows the near field intensity distribution (a) and the far field intensity distribution (b) of a multi-mode emitter for application in a skin treatment device according to an embodiment of the invention. The laser light emitted by a single mode emitter is nominally a TE00 mode beam (only one mode present being typically TE00) with a Gaussian intensity distribution and behaving according to the principles of Gaussian beam propagation. Therefore, these beams have Gaussian beam profiles both in the near field and far field. The laser light is typically emitted by the emitting aperture in a cone larger than 40° F.WHM (Full Width Half Maximum) resulting in a highly divergent beam (typically over a much larger NA of approximately 0.63). Therefore, when multiple single modes are closely spaced, the resulting beam profile will smear out and will not result in a non-uniform intensity distribution with ripples as shown in FIG. 3, as emitted by an array of multi-mode emitters or lasers.

Typically, laser light emitted by a multi-mode light source is a superposition of multiple modes (including TE00 and other higher-order modes) having a very non-Gaussian angular beam profile with ripples (both macro- and micro-spatial non-uniformities) as shown in FIG. 9 (a). Such multi-mode lasers have long and narrow emitting apertures, and typically the light is emitted by the emitting aperture in a cone smaller than 10° F.WHM (Full Width Half Maximum) and in a relatively small NA of 0.13. These beams do not follow principles of Gaussian beam propagation. Because of the lower divergence of the beam, a non-uniform beam profile will be substantially maintained, as compared to single mode emitters. In the far field, the beam profile tends to be bimodal with a pronounced dip in the center.

Another way of expressing the difference between single-mode and multi-mode array emitters is in terms of Lagrange value (H). The Lagrange value of the laser beam is commonly defined as the product of half the beam size and half the divergence angle. This Lagrange value of a multi-mode emitter is much larger than that of a single-mode emitter. For a representative emission wavelength of 0.83µ (micrometer), the Lagrange value of a single-mode emitter is 0.09µ (micrometer) and that of a multi-mode emitter is typically 7µ (micrometer).

The light source is typically a pulsed laser, for example, a diode laser with an emission wavelength that matches the specific skin chromophore (water), typically around 1000-2000 nm, preferably between 1300 and 1700 nm, and that is shorter than the thermal relaxation of the targeted dermis or chromophore and that is in the range of 0.1-200 ms pulse duration and preferably between 5 and 20 ms. This will lead to high temperatures in the range of 60-100° C., preferably between 70 and 90° C. in the central zones and low-temperatures in the range of 39-50° C., preferably between 40 and 45° C. in the surrounding tissue.

The peak fluence in the central zones is in the range of 10-20 $J/cm^2$, whereas the peak fluence in the surrounding zones is in the range of 1-2 $J/cm^2$. This leads to central zones of collagen denaturation and shrinkage surrounded by zones of fibroblast stimulation. The ratio of the fluence in the high-intensity zones 30 to that in the surrounding low-intensity zones 40 can be in the range of 2-50 and preferably in the range of 5-10.

The output beam can have a pulse duration between 0.1 and 100 milliseconds, and preferably between about 1 and 5 milliseconds. The radiation source 5 and the skin treatment device 10 can also be configured to provide similar lesions, but these are spatially confined in the dermis and surrounded by zones of fibroblast stimulation (cf. FIG. 6.d) by using focusing optics and imaging the emitter plane into the dermis 103, which will maintain the irradiance profile in the dermis. In this case, the treatment location in the inner dermal layer will be determined by suitably located chromophores such as melanin, sebaceous glands, blood vessels, which are irradiated by the treatment beam and a selective temperature rise will occur at the isolated selective targets.

The technical features required to achieve the above mentioned result of non-ablative central zones of collagen denaturation surrounded by thermal zones of fibroblast stimulated tissue can be broadly classified into two categories depending on whether a single or multiple emitters are needed to get this intensity profile.

The first category comprises a non-uniform intensity profile, wherein use is made of a single emitter. This could be realized by tuning the laser cavity to emit a superposition of three Hermite-Gaussian (HG) modes, cf. FIGS. 10 and 11. In this case a single emitter can provide the above-mentioned result.

Figure 10:
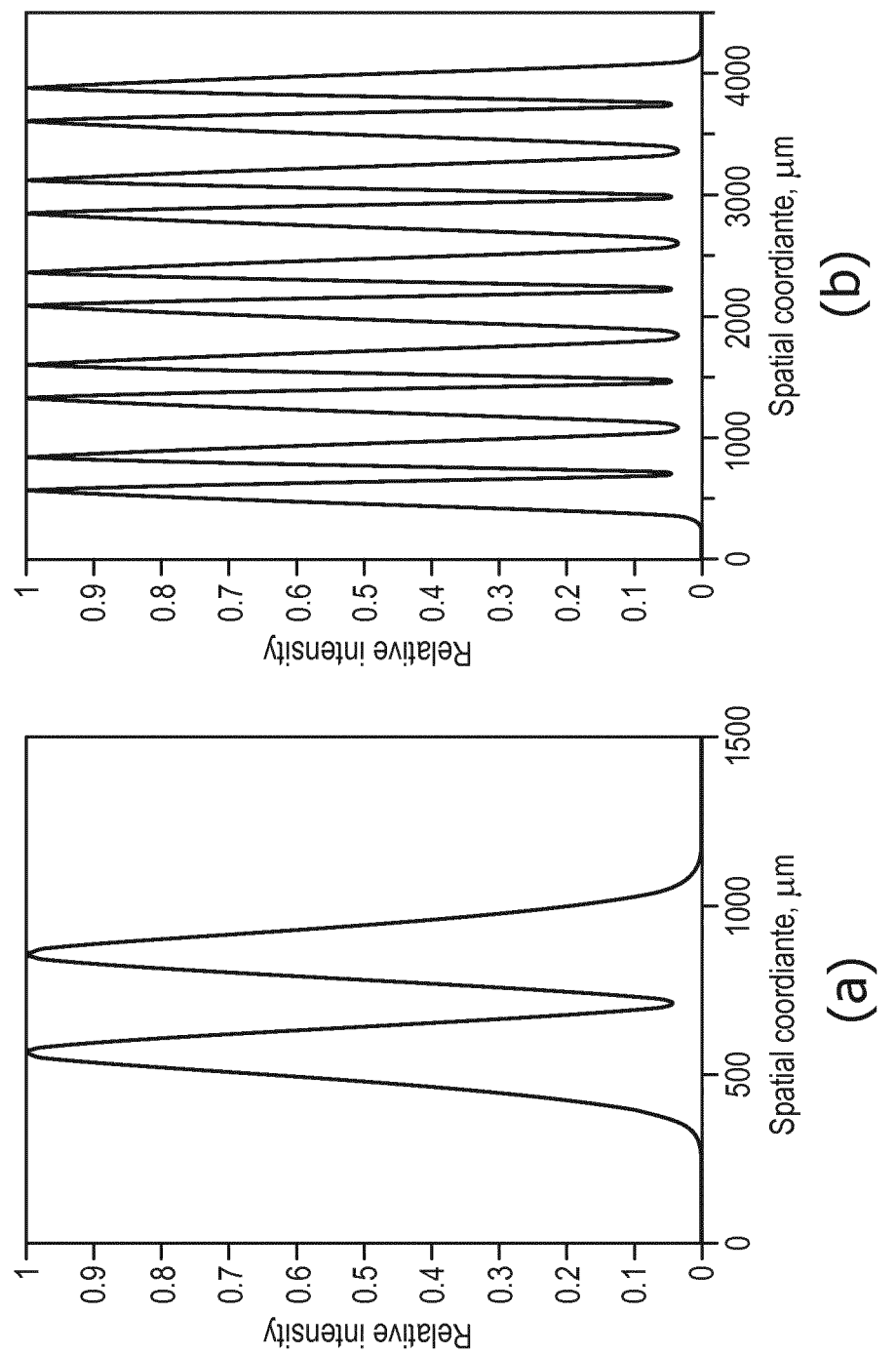
FIG. 10 shows (a) the line profile of intensity from one multi-mode light source which emits a superposition of three higher-order modes (HG12+HG21+HG22), and (b) the resulting intensity distribution of an array of five multi-mode laser sources placed next to each other for large area treatment.

FIG. 10 shows (a) the line profile of intensity from one multi-mode light source which emits a superposition of three higher-order modes (HG12+HG21+HG22), and (b) the resulting intensity distribution of an array of five multi-mode laser sources placed next to each other for large area treatment.

Figure 11:
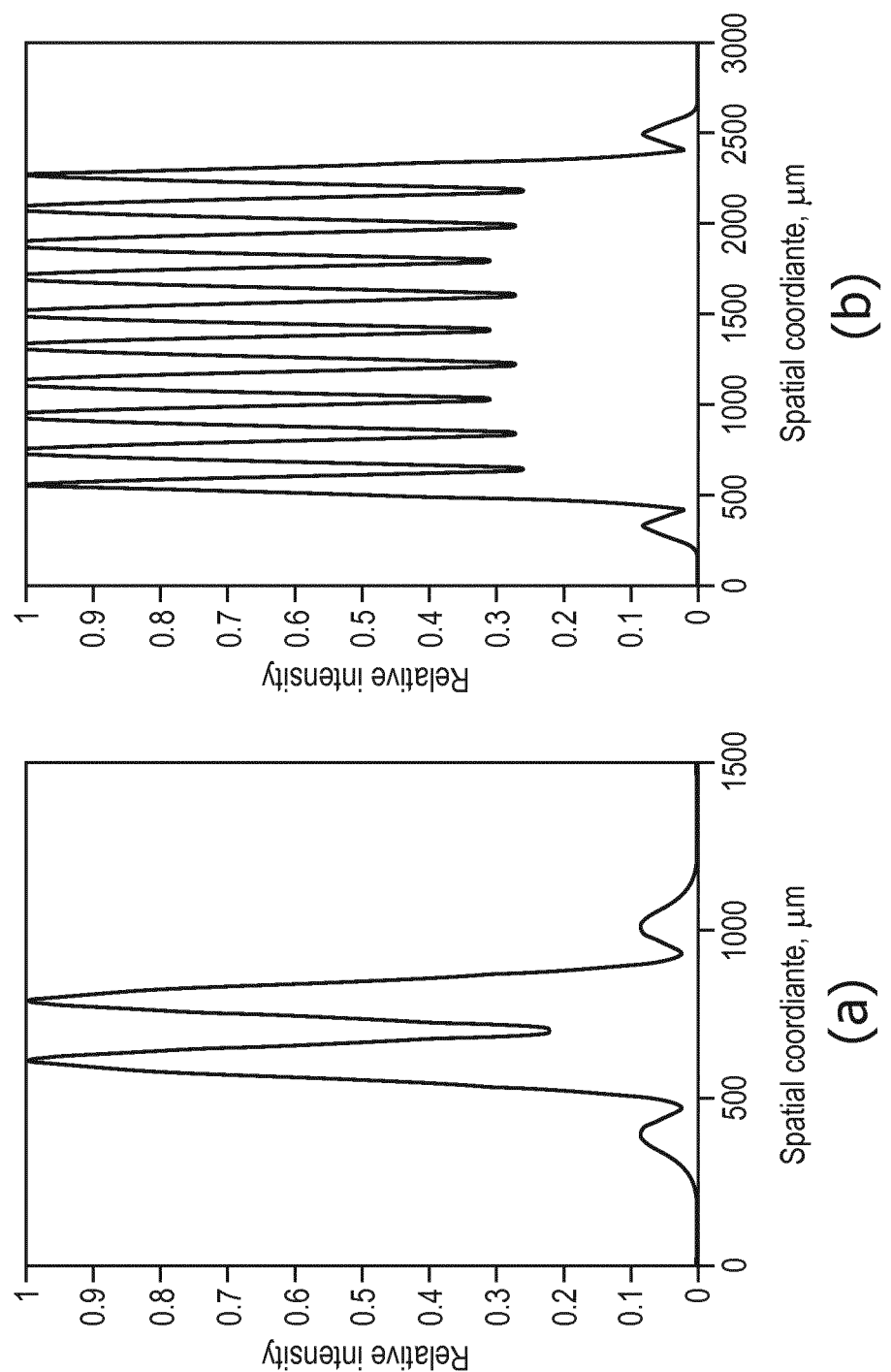
FIG. 11 shows (a) the line profile of intensity from one multi-mode light source which emits a superposition of three higher-order modes (HG32+HG23+HG33), and (b) the resulting intensity distribution of an array of five multi-mode laser sources placed next to each other for large area treatment.

FIG. 11 shows (a) the line profile of intensity from one multi-mode light source which emits superposition of three higher-order modes (HG32+HG23+HG33), and (b) the resulting intensity distribution of an array of five multi-mode laser sources placed next to each other for large area treatment.

The second category comprises a non-uniform intensity profile obtained by using more than one emitter, i.e. an array of lasers in the radiation source 5. This could be realized by tuning the laser cavity to emit a superposition of three Hermite-Gaussian (HG) modes, cf. FIG. 12. In this case, a single emitter cannot provide the above mentioned result. However, by placing a second laser emitter next to it, the desired intensity profile can be obtained, e.g: HG23+HG13+HG22.

The output beam can have a pulse duration between 0.1 and 100 milliseconds, and preferably between about 1 and 5 milliseconds. For a pulse duration shorter than the thermal relaxation time, thermal confinement may occur within the illuminated zones.

In general, the required superposition of multiple higher-order HG modes is obtained using the general laser manufacturing process by proper misalignment of a laser cavity (with a Brewster window), selectively disabling parts of the gain medium or by using an astigmatic mode converter, or other similar methods in laser optics the skilled person would readily realize.

Figure 12:
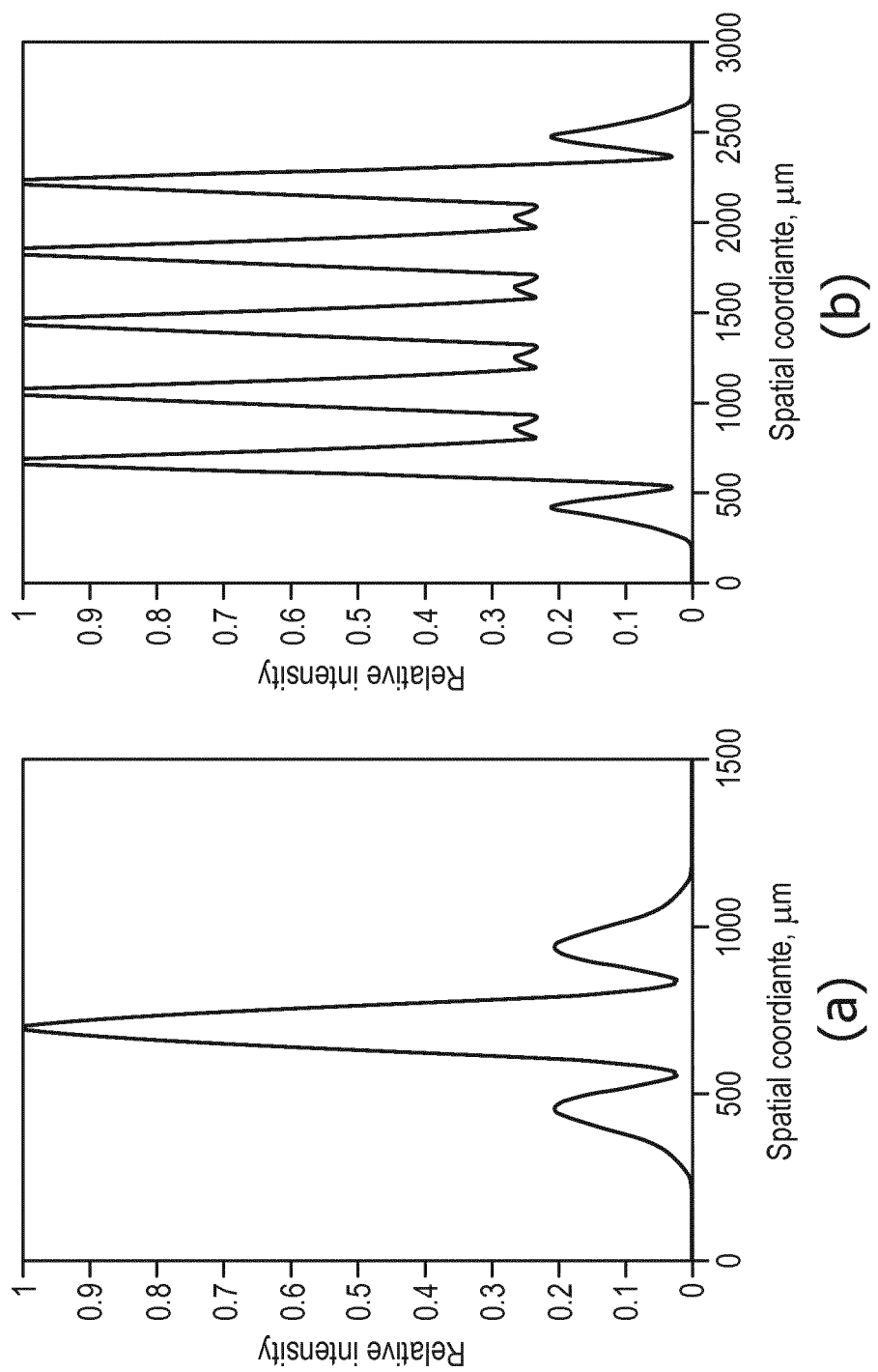
FIG. 12 shows (a) the line profile of intensity from one multi-mode light source which emits a superposition of three higher-order modes (HG23+HG13+HG22), and (b) the resulting intensity distribution of an array of five multi-mode laser sources placed next to each other for large area treatment, and FIG. 13 schematically shows a flow diagram for a method for skin treatment.

FIG. 12 shows (a) the line profile of intensity from one multi-mode light source which emits a superposition of three higher-order modes (HG23+HG13+HG22), and (b) the resulting intensity distribution of an array of five multi-mode laser sources placed next to each other for large area treatment.

Some simulations were performed to find the possible options of using a multiple number of modes (N), and also to identify the preferred options. In short, multiple solutions are possible for this application by choosing higher mode order numbers (HGmn), where m and n represents the mode numbers. However, the relative amount of power that will be available in the higher-order modes will be significantly reduced as the order number becomes higher, thereby limiting the preferred options of m, n<4, alternatively 6 or 8.

In addition to the above mentioned point, the following aspects need to be taken into further consideration:
1. The low-order modes are preferable, because of a smooth intensity profile and low divergence.

2. The primary method for reducing the unwanted modes is to add sufficient loss to them. In most lasers, this is accomplished by placing a fixed or variable aperture inside the laser cavity. Because of the significant differences in beam diameter, the aperture can cause significant diffraction losses for the higher-order modes without impacting the lower-order modes.

Based on these estimates, the preferred options for each category are summarized as follows for HG configuration of modes:

Single Laser Emitters:
1. N=3 (HG21+HG22+HG12)
2. N=2 (HG23+HG32)
3. N=3 (HG31+HG13+HG22, HG32+HG23+HG33)
4. N=4 (HG31+HG13+HG33+HG22)

Multiple Laser Emitters:
1. N=3 (HG23+HG13+HG22)
2. N=2 (HG24+HG42)
3. N=3 (HG24+HG42+HG33)
4. N=4 (HG24+HG52+HG33+HG42)

Comparing the two categories of single and multiple emitters, preference would be given to single emitters.

For the category of multiple laser emitters, each of the emitters should be emitting an identical number and types of modes.

The required superposition of multiple HG modes may be obtained using the general laser manufacturing process by proper misalignment of a laser cavity (with a Brewster window), selectively disabling parts of the gain medium or by an astigmatic mode converter, which is cheaper than getting single mode laser beams.

Figure 13:
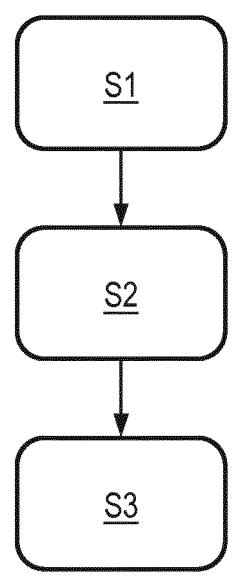

FIG. 13 schematically shows a flow diagram for a method for non-invasive skin treatment, in particular fractional treatment of the skin 100 of a human being, cf. FIG. 1, the skin treatment method comprising the below steps, which need not be performed in the listed order;

S1: providing a radiation source 5 capable of emitting a multi-mode laser beam 20, the laser beam having a superposition 23 of at least two different higher-order laser modes, the laser modes having mutually different intensity profiles, 21 and 22, in a beam cross-section transverse to a propagation direction of the laser beam, and S2: providing a radiation control unit 6 for controlling the radiation source, S3: wherein the radiation source and the radiation control unit are optically arranged so that the multi-mode laser beam, when impinging on a treatment zone 50 of the skin, is spatially configured by said superposition 23 of said higher-order laser modes so as to simultaneously cause:
  a first plurality of high-intensity zones 30, wherein the thermal threshold (TC) for collagen denaturation for said treatment zone of the skin is at least reached, and
  a second plurality of low-intensity zones 40, wherein the thermal threshold (TF) for fibroblast stimulation for said treatment zone of the skin is at least reached, but wherein said thermal threshold (TC) for collagen denaturation is not reached.

In short, the invention relates to a skin treatment device 10 for fractional treatment of the skin 100 of a human being, as for example shown in FIG. 1. A radiation source 5 emits a multi-mode laser beam 20 substantially only comprising a superposition 23 of only higher-order laser modes which are mutually different. The multi-mode laser beam is configured by said superposition of different laser modes to simultaneously cause a first plurality of high-intensity zones, where the thermal threshold (TC) for collagen denaturation for the treatment zone 50 of the skin is at least reached, and a second plurality of low-intensity zones where the thermal threshold (TF) for fibroblast stimulation for the treatment zone of the skin is at least reached, cf. FIG. 4. This is advantageous for obtaining a skin treatment device with a simple and therefore low-cost fractional laser skin treatment system for combined collagen denaturation and fibroblast stimulation. The skin treatment device is based on non-uniform laser radiation in the form of the multi-mode laser beam.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A skin treatment device for fractional treatment of the skin of a human being, the skin treatment device comprising:
   a radiation source capable of emitting a multi-mode laser beam,
   a lens for directing the multi-mode laser beam onto the skin, and
   a processor for controlling the radiation source,
such that the multi-mode laser beam, when impinging on a treatment zone of the skin, is spatially configured so as to simultaneously create:
   a first plurality of high-intensity zones wherein a thermal threshold (TC) for collagen denaturation for said treatment zone of the skin is at least reached, and
   a second plurality of low-intensity zones wherein a thermal threshold (TF) for fibroblast stimulation for said treatment zone of the skin is at least reached, but wherein said thermal threshold (TC) for collagen denaturation is not reached,
wherein the multi-mode laser beam substantially only comprises a superposition of only higher-order laser modes which are mutually different, the higher-order laser modes having mutually different intensity profiles in a beam cross-section transverse to a propagation direction of the laser beam, wherein the radiation source is configured so that a Lagrange value (H) of the multi-mode laser beam, when leaving the lens, is at least 0.5 μm.

2. The skin treatment device according to claim 1, wherein the superposition of higher-order laser modes results in a combined intensity profile of the multi-mode laser beam, with one, or more, non-zero minima (MIN) corresponding to one, or more, low-intensity zones in said second plurality of low-intensity zones.

3. The skin treatment device according to claim 1, wherein the superposition of higher-order laser modes results in a combined intensity profile of the multi-mode laser beam, with one, or more, maxima (MAX) corresponding to one, or more, high-intensity zones in said first plurality of high-intensity zones.

4. The skin treatment device according to claim 1, wherein the multi-mode laser beam, when impinging on the treatment zone of the skin, is spatially configured by said superposition of higher-order laser modes so as to form a coherent treatment zone of the skin.

5. The skin treatment device according to claim 4, wherein the thermal threshold (TF) for fibroblast stimulation is at least reached substantially throughout said coherent treatment zone of the skin.

6. The skin treatment device according to claim 1, wherein the first plurality of high-intensity zones and the second plurality of low-intensity zones are spatially distributed in the treatment zone so that, when the multi-mode laser beam impinges on the treatment zone of the skin, a thermal profile is induced wherein the temperature gradually decreases from the high-intensity zones to any neighboring low-intensity zones surrounding the high-intensity zones, and wherein the temperature continuously decreases from the high-intensity zones to the neighboring low-intensity zones.

7. The skin treatment device according to claim 1, wherein the radiation source is configured so that a number (N) of the different higher-order laser modes of the superposition is at most 10.

8. The skin treatment device according to claim 1, further comprising a lens for directing the multi-mode laser beam onto the skin, wherein the radiation source is arranged so that a maximum spatial extension of the treatment zone is at least 10 mm.

9. The skin treatment device according to claim 1, wherein said superposition comprises at least two mutually different higher-order laser modes selected from:
   rectangular transverse Hermite-Gaussian modes HG[m n], wherein m and n are mode numbers, or
   cylindrical transverse Laguerre-Gaussian modes LG[p l], wherein p and l are mode numbers, and wherein each of the mode numbers, [m n] or [p l], is below 8.

10. The skin treatment device according to claim 1, wherein the radiation source comprises a plurality of lasers controllable by the processor, each laser being capable of emitting a multi-mode laser beam, each multi-mode laser beam substantially only comprising a superposition of only higher-order laser modes with mutually different intensity profiles in a beam cross-section transverse to a propagation direction of the laser beam.

11. The skin treatment device according to claim 10, further comprising a lens for directing the multi-mode laser beams onto the skin, wherein the laser beams emitted from the plurality of lasers have a common optical path from the radiation source to the lens.

12. The skin treatment device according to claim 10, wherein the plurality of lasers controllable by the processor are optically arranged so as to create a common treatment zone in the skin, or wherein the plurality of lasers controllable by the processor are optically arranged to create at least two different treatment zones in the skin, each treatment zone having
   a first plurality of high-intensity zones wherein the thermal threshold (TC) for collagen denaturation for said treatment zone of the skin is at least reached, and
   a second plurality of low-intensity zones wherein the thermal threshold (TF) for fibroblast stimulation for said treatment zone of the skin is at least reached, but wherein said thermal threshold (TC) for collagen denaturation is not reached.

13. The skin treatment device according to claim 1, wherein the radiation source comprises a single laser capable of emitting a multi-mode laser beam, the laser beam substantially only comprising a superposition of only higher-order laser modes which are mutually different, the higher-order laser modes having mutually different intensity profiles in a beam cross-section transverse to a propagation direction of the laser beam.

* * * * *